United States Patent [19]

Quinn, III

[11] 4,047,307

[45] Sept. 13, 1977

[54] SNAP ACTION FRAME FOR FACIAL IDENTIFICATION SYSTEM

[76] Inventor: William T. Quinn, III, 681 Park Ave., Freehold, N.J. 07728

[21] Appl. No.: 690,812

[22] Filed: May 27, 1976

[51] Int. Cl.² .............................................. G09B 1/30
[52] U.S. Cl. ....................................... 35/28; 24/67.5; 40/10 D
[58] Field of Search .................... 24/67.3, 67.5; 35/28, 35/62, 26; 40/10 D, 13, 155

[56] References Cited

U.S. PATENT DOCUMENTS

| 761,033 | 5/1904 | Cross ................................ 35/26 UX |
| 908,170 | 12/1908 | Van Der Boom .................... 40/155 |
| 1,593,724 | 7/1926 | Schenk ................................... 40/13 |
| 1,705,564 | 3/1929 | Ginsberg ............................... 40/13 |

FOREIGN PATENT DOCUMENTS 1,137,088  12/1968  United Kingdom ..................... 35/28

OTHER PUBLICATIONS

W. R. Hopper, "Photo-Fit-The Penry Facial Identification Technique", J. Forensic Sci. Soc. (1973) pp. 77-79 only.

Primary Examiner—Harland S. Skogquist
Attorney, Agent, or Firm—Sughrue, Rothwell, Mion, Zinn and Macpeak

[57] ABSTRACT

A frame for a facial identification system of the type wherein changeable facial feature components are assembled to create a representaton of a face includes a base member with an elevated ledge along one side thereof. A transparent cover plate overlies a portion of the base member, and snap hinges extend between the ledge and the cover plate. Vertical and horizontal indicia on exposed portions of the base member provide coordinates for specification of location of facial features.

1 Claim, 2 Drawing Figures

SNAP ACTION FRAME FOR FACIAL IDENTIFICATION SYSTEM

BACKGROUND OF THE INVENTION:

1. Field of the Invention

This invention pertains to a frame for holding changeable components of a facial feature identification system.

2. Statement of the Prior Art:

In my prior U.S. Pat. No. 3,896,565, a facial identification system of the general category involved here is shown. Similarly, my prior application Ser. No. 599,484, now U.S. Pat. No. 3,974,576, illustrates another similar arrangement.

SUMMARY OF THE INVENTION

A principal objective of the invention hereof resides in the provision of a frame or holder for the components of a facial identification system which has snap action hinges to positively lock the components in place, and to obviate the possibility of disarray of the components after assembly and during handling of the frame. This is important in the case of a system of this nature in that the recall of witnesses to an event may be seriously hampered if, during exhibit of an assembled composite of the suspected subject, the materials fall into a state of disarray.

Another objective of significance relates to the provision of a grid coordinate system in the form of indicia inscribed on the unit. Such coordinate system permits the specification of location of features such as scars, moles, etc. The system hereof contemplates that numerous police departments or other investigative agencies will be provided with duplicate frames and sets of components. Thus, with the components having numerical or other identifications thereon, it is possible to specify to a remote location a made-up drawing of an individual, and through the coordinates, to accurately place a scar or the like on a composite drawing.

The frame cover plate is at least partially transparent, and may be marked upon to inscribe said features.

Other and further objects and advantages of the invention will become apparent to those skilled in the art from a consideration of the following specification when read in conjunction with the annexed drawing.

DESCRIPTION OF THE PREFERRED EMBODIMENT

Figure 1:
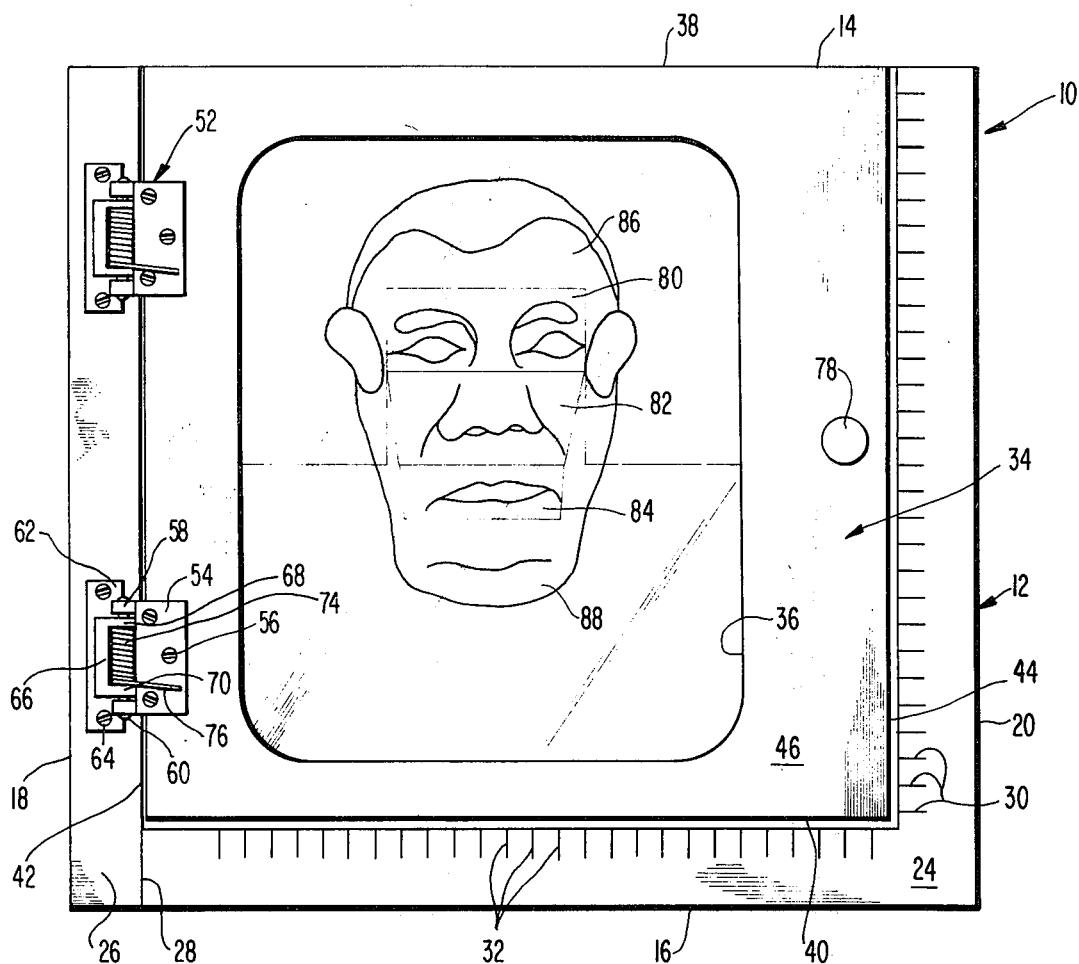
FIG. 1 is a plan view of a snap action frame in the system of the type contemplated in this invention.
Figure 2:
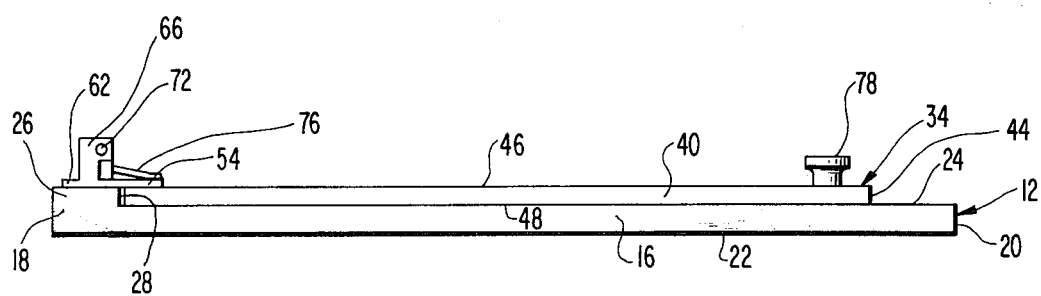
FIG. 2 is a bottom end elevational view thereof.

Referring to the drawing in more detail, the frame hereof is generally identified therein by reference numeral 10. The frame 10 comprises a base member 12 preferably of opaque material and having top and bottom edges 14, 16, and side edges 18 and 20. The base member further has a lower surface 22 and an opposite upper surface 24.

Extending along the side 18 of the base member is an integrally formed, elevated ledge 26. The ledge has an inside wall 28.

As shown in FIG. 1, inscribed or otherwise marked on the top surface 24 of the base member adjacent the side edge 20 is a series of first indicia 30. Similarly, second indicia 32 extend in linear fashion along the top surface adjacent the bottom edge 16. Together, the first and second indicia provide a grid coordinate system.

A cover plate 34 has a transparent central section 36 and includes upper and lower edges 38, 40 and first and second side edges 42, 44. The plate also has top and inside surfaces 46, 48. The first side edge 42 of the cover plate is located adjacent and parallel to the wall 28 of the ledge. The second edge 44 is spaced inwardly from the side edge 20 of the base member whereby the series of first indicia 30 is exposed. The upper edge 38 of the cover plate is vertically aligned with the top edge 14 of the base member, but the lower edge 40 is spaced inwardly from the bottom edge 16 whereby the second series of indicia 32 are exposed.

A pair of snap hinge assemblies 52 are provided. Each has a hinge plate 54 secured to the cover plate by screws 56 or the like. Sleeves 58 and 60 extend from the hinge plate over the ledge, and hinge bases 62 are secured on the ledge by screws 64. A bracket 66 projects upwardly from each hinge base, and has inward arms 68, 70. A hinge pin 72 extends through the sleeves 58, 60 and arms 68, 70, and has a coil spring 74 thereabout, with a spring arm 76 extended over the hinge plate 54 and constantly biasing the cover plate to clamping position with its inside surface 48 flush against the upper surface 24 of the base. Lifting of the cover plate against the tension of the spring with a handle 78 exposes the base for placement of articles thereon.

In operation, the various component segments, such as an eye segment 80, nose segment 82, mouth segment 84, and forehead and chin segments 86, 88, are assembled on the face, and the cover plate snapped to closed position thereby fixing the segments in place. Any other features, such as scars or moles, may be added by marking the same on the cover plate with a non-indelible marker or the like in accordance with a location supplied by witnesses and transmitted to other authorities via reference to the grid coordinate system.

The base member 12 is provided with positioning elements for uniform alignment of the components.

I claim:

1. In a facial identification system comprising a composite of facial features interrelated to form a representation of a subject, the composite being made up from changeable individual feature component segments, a holder for said segments comprises:

a base member having top and bottom edges, side edges, and a lower surface;

an elevated ledge along one of said side edges, the ledge extending inwardly;

the base member having an upper surface opposite said lower surface;

first indicia on the upper surface adjacent the side edge remote from the elevated ledge;

second indicia on the upper surface adjacent the bottom edge;

the first and second indicia cooperatively providing coordinates for definition of the location of characteristics on said representation;

a transparent cover plate having upper and lower edges and first and second side edges;

the cover plate having top and inside surfaces;

the first side edge of the cover plate being located adjacent the elevated ledge, and the second side edge being spaced inwardly from the side edge of the base member having said first indicia whereby said indicia are exposed;

the upper edge of the cover plate being vertically aligned with the top edge of the base member, and the lower edge of the cover plate being spaced inwardly from the bottom edge of the base member whereby the second indicia are exposed; and snap hinges on the ledge and cover plate to effect flush fitting relationship between the cover plate and base member and to clamp said representations firmly therebetween, said hinges each comprising a hinge plate on the cover plate having sleeves extended therefrom over the elevated ledge, hinge bases on the ledge with a bracket, hinge pins extending through the brackets and sleeves, and springs within the brackets and about the pins and having spring arms extended over the hinge plates.

* * * * *